United States Patent
Prather

(10) Patent No.: US 6,443,434 B1
(45) Date of Patent: Sep. 3, 2002

(54) FORCED-AIR SCENT DISPENSER

(76) Inventor: Jimmy D. Prather, 191 Country Hill Cir., Sherman, TX (US) 75090

( * ) Notice: Subject to any disclaimer, the term of this patent is extended or adjusted under 35 U.S.C. 154(b) by 0 days.

(21) Appl. No.: 09/618,929

(22) Filed: Jul. 18, 2000

(51) Int. Cl.[7] .................................................. B01F 3/04
(52) U.S. Cl. ............................ 261/26; 261/30; 261/76; 261/142; 261/DIG. 88; 261/DIG. 89; 422/124; 43/1; 43/129
(58) Field of Search ........................... 261/26, 30, 142, 261/DIG. 88, DIG. 89, 76, 77; 422/124; 43/1, 129

(56) References Cited

U.S. PATENT DOCUMENTS

| | | | | |
|---|---|---|---|---|
| 4,771,563 A | * | 9/1988 | Easley | 43/1 |
| 5,029,729 A | * | 7/1991 | Madsen et al. | 422/124 |
| 5,970,643 A | * | 10/1999 | Gawel, Jr. | 43/1 |
| 6,050,016 A | * | 4/2000 | Cox | 43/1 |
| 6,264,895 B1 | * | 7/2001 | Johnson | 34/80 |

* cited by examiner

Primary Examiner—Robert A. Hopkins
(74) Attorney, Agent, or Firm—Michael L. Diaz

(57) ABSTRACT

A dispenser for scents used to attract deer and other animals includes a housing with an intake on one end and an exhaust on the other. Inside the housing is a timing circuit which controls a cyclic heater element. The heater element is positioned to transfer heat to a bottle of liquid scent. As the scent is warmed, its evaporation increases so that the vaporized scent escapes from the bottle. A low-voltage fan pulls air into the container through the inlet and blows it out the exhaust vent, carrying with it the scent vapor. A timing circuit causes the heater and fan to cycle on and off at predetermined intervals, and the timing circuit may be controlled by a wireless remote control unit. Power to the heater and fan is supplied by a rechargeable battery.

10 Claims, 2 Drawing Sheets

FORCED-AIR SCENT DISPENSER

CROSS REFERENCE TO RELATED APPLICATIONS

Not Applicable.

BACKGROUND OF THE INVENTION

1. Field of the Invention

This invention relates to devices for dispensing scent into the atmosphere to attract animals, and in particular to such dispensers which release scents to attract deer.

2. Description of the Related Art

Deer hunting is a sport enjoyed by thousands of men and women across the country. In some parts of the country, deer are hunted from stands or blinds, from which vantage point the hunter waits for an opportunity for a shot. This type of hunting is usually practiced in wooded a areas or partially wooded areas. That is, the deer are usually relatively near the hunter, as compared to hunting in more open country. When hunting from a stand, a hunter may wait for a deer to come into view, or he may use means such as scents to attract deer to within his field of fire.

Attracting deer with scents is well known. Different types of scents have been used for many years with mixed results. In recent years, more successful scents or lures have been developed; these are primarily derived from deer urine. Different scents are attractive to bucks and does, and the particular scent chosen by a hunter will be determined by the type of game is trying to attract.

SUMMARY OF THE INVENTION

The invention is a forced air dispenser for scents used to attract animals. The invention is described primarily in terms of scents used to attract deer, but is equally applicable to dispensing scents to attract other animals. A housing has an air intake at one end and an outlet at the other. Inside the housing are a battery, a timer circuit, a fan, and a container for liquid scent. Evaporation of the liquid scent is increased by heating the liquid to about 150°–160° F. Scent vapor is mixed with air as the air is forced through the housing by the fan; the scent-laden air is blown out into the surroundings via the outlet. An auxiliary solar panel is provided to recharge the battery in remote locations. Alternatively the battery may be recharged from another source of power.

Based on the above, it is an object of this invention to provide a self contained, forced-air dispenser for scents.

A further object is to provide a scent dispenser which efficiently uses liquid scents.

Another object is to provide a scent dispenser which operates quietly while broadcasting the scent over a wide area.

Further objects are to achieve the above with a device that is compact, durable, simple, efficient, reliable, yet inexpensive and easy to operate.

The specific nature of the invention, as well as other objects, uses, and advantages thereof, will clearly appear from the following description and from the accompanying drawings, the different views of which are not necessarily scale drawings.

CATALOG OF THE ELEMENTS

Figure 1:
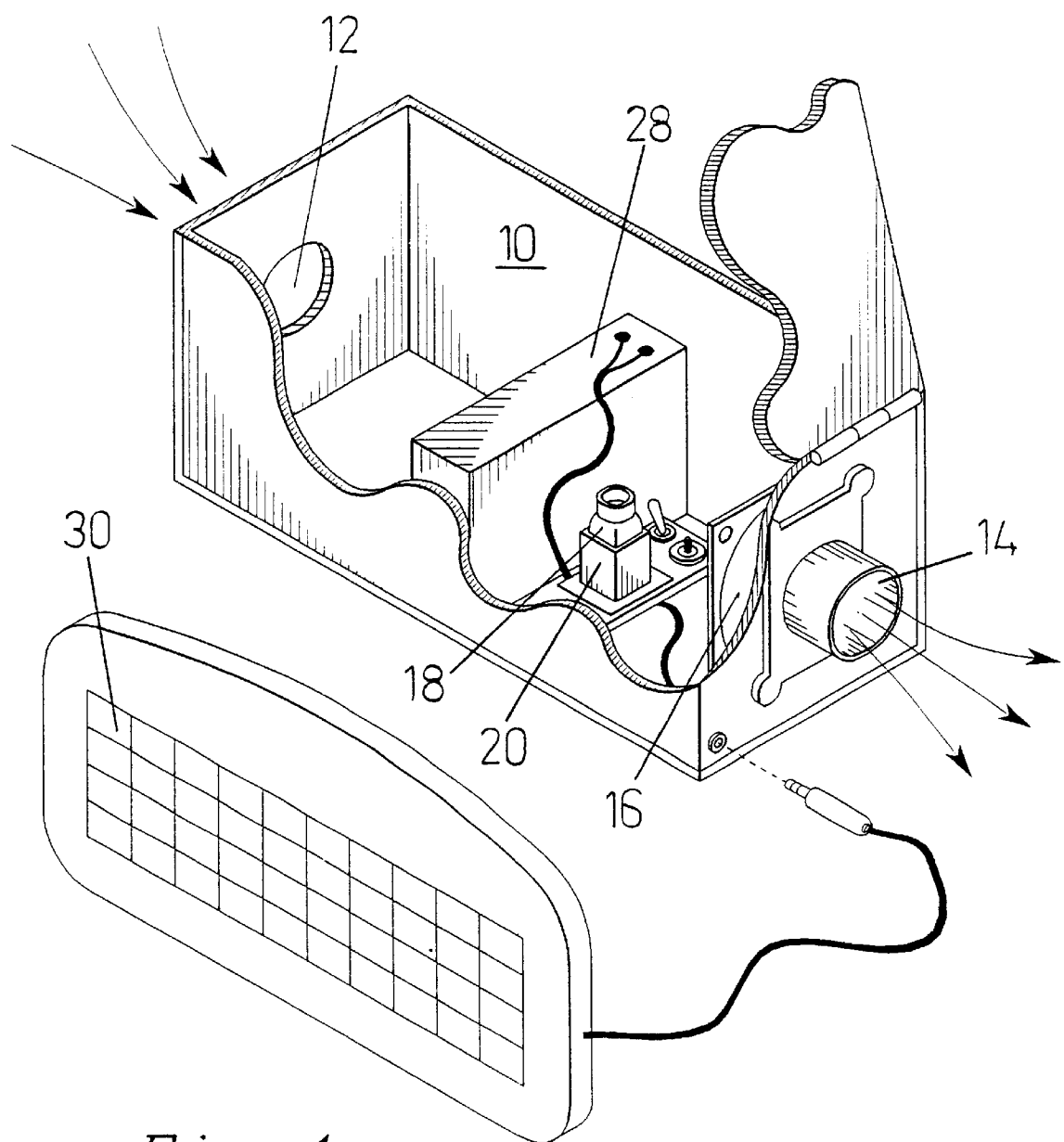
FIG. 1 is a cutaway view of the scent dispenser showing the elements of the invention.
Figure 2:
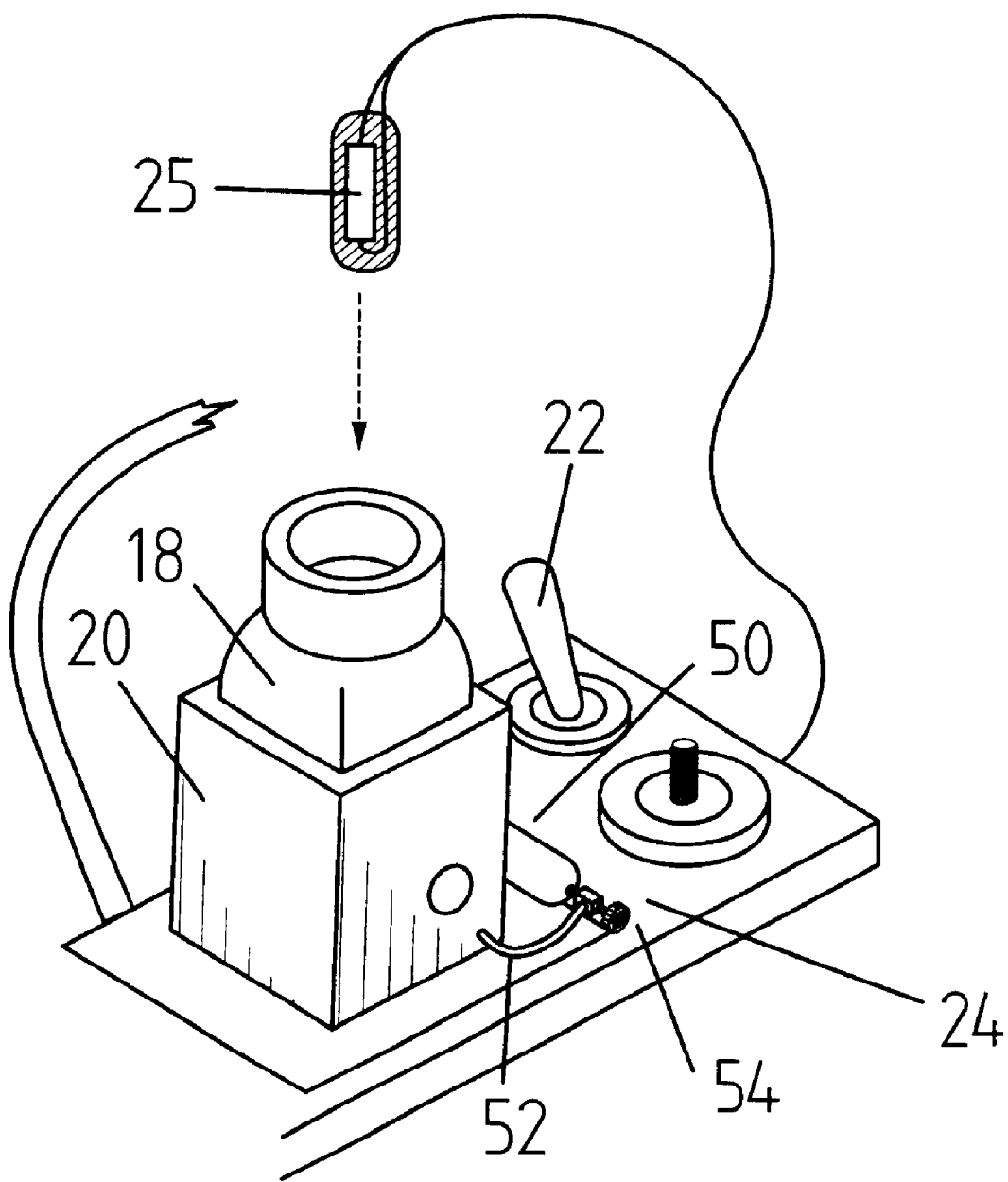
FIG. 2 is an elevation of the scent dispenser housing, showing the air intake, the exhaust, and auxiliary solar panel.

To aid in the correlation of the elements of the invention to the exemplary drawings, the following catalog of the elements is provided:

10 housing
12 air intake
14 air exhaust
16 fan
18 scent container
20 container holder
22 on-off switch
24 circuit board
25 heating element
28 battery
30 solar panel

DESCRIPTION OF THE PREFERRED EMBODIMENTS

Referring now to the drawings, FIG. 1 discloses a dispenser for airborne scents. The dispenser includes a housing 10 with an air intake 12 and an outlet 14. Generally rectangular in cross section, the housing 10 is made of molded or blown plastic, and has an openable cover. A hinged cover is shown in the accompanying drawings, but it is understood that the cover may be completely removeable from the housing. Latches secure the cover in place on the housing.

Inside the housing is a circuit board 24 which includes circuitry for a timer circuit. Circuit board 24 is mounted on or near the floor of housing 10. Attached to the circuit board, or mounted nearby, is a holder 20 for a container 18 of liquid scent. Holder 20 is an open-topped receptacle have a shape and dimensions suited to holding a small bottle of liquid scent.

In one embodiment of the invention, the heating element 25, i.e., an electrical resistor, is located on the circuit board 24 beneath the scent container 18. Where the heating element 25 is located beneath the scent container, a 15 ohm, 5 watt resistor is used for the element. In another embodiment, the heating element is connected to wiring having enough slack therein for the heating element to be inserted into the liquid scent through the open top of the scent container 18. In this latter embodiment, the heating element is a resistor encased in a water-proof coating; the water-proof coating is applied by a suitable method, including dipping the resistor into a liquid water-proofing compound, or forming a layer of water-proof putty around the resistor. For the immersible heating element, the resistor used is 27 ohm, 5 watt. In either case, the liquid is heated to about 150–160° degrees, with lesser battery drain being the advantage of the larger resistor used in the immersible heating element. A third embodiment of the heater assembly includes electrical leads to the resistor which are led through an opening the bottom of the scent container. The opening through which the leads pass is sealed with epoxy or other suitable sealer. This configuration ensures that the resistor remains in place at the bottom of the container where it most efficiently heats the liquid scent.

Switch 22 activates an electronic circuit which includes a timer. The timer causes the circuitry to cycle between "on" and "off" conditions. Timing of the cycle is variable; a cycle of one minute on and three minutes off has proven effective in use. Intervals between "on" portions of the cycle, and the length of the "on" portion of the cycle may be adjustable by a user, or may be pre-set with no provision for adjustment.

As may be seen from the drawing in FIG. 1, air is pulled into the housing 10 through the inlet 12 by the fan 16, and then exits through the outlet 14. Fan 16 is a compact fan which draws a low current, but effectively moves a stream of air through the dispenser housing. Inside the housing, incoming air is mixed with vapor from the heated scent, so that molecules of scent are blown out the exhaust with the air flow.

Another embodiment of the invention increases the rate of vaporization of the liquid scent by injecting a gas into the liquid. The resultant bubbles rise to the surface of the liquid, where the thin film of liquid surrounding the bubbles evaporates. This evaporation speeds dispersal of the scent into the air flow through the dispenser housing. Gas, such as $CO_2$, for producing bubbles is provided from a cylinder 50 contained within the housing. The cylinder feeds gas into a conduit 52 which opens near the bottom of the scent container. Release of the gas is controlled by a valve 54 in the gas conduit; the valve can be electromechanical, and can be controlled remotely by a remote control unit as described above.

A rechargeable battery 28 is mounted within the housing to provide current for the timer the heating element, and the fan. In the preferred embodiment, the battery is rechargeable and has a 12 volt output. Part of the circuitry on the printed circuit board is a battery protection circuit, which turns off power to the circuits when the battery output drops below about 11 volts. Also provided is a remote control unit which, by means of infra-red or other suitable signal, turns the scent dispenser on or off. By using the remote control unit, a hunter may set up the scent dispenser for later use; i.e., the hunter can place the scent dispenser in position and then turn it on later, after he has reached his stand or blind.

In use, a hunter takes the scent dispenser with him into the hunt area and places it in a suitable location to attract deer. Different scents may be used; some scents are to attract bucks, and some attract does. After reaching his hunting location the hunter unlatches the housing cover and reaches in to activate the on-off switch. With the switch in the on position, the timer causes the fan and heater to operate at regular intervals. As the fan pulls air through the inlet, the scent vapor is mixed with the air and blown out through the exhaust.

Because the fan forces air through the housing the liquid scent is used more sparingly and is broadcast over a wider area. Thus, operation of the fan results in a more efficient use of liquid scent.

The restrictive description and drawings of the specific examples above do not point out what an infringement of this patent would be, but are to enable one skilled in the art to make and use the invention. Various modifications can be made in the construction, material, arrangement, and operation, and still be within the scope of my invention. The limits of the invention and the bounds of the patent protection are measured by and defined in the following claims.

What is claimed is:

1. A dispenser for scents used to attract animals, comprising:

a housing, an air inlet into said housing, an exhaust from said housing, a holder for receiving a container of liquid scent, means for heating the liquid scent, said means for heating the liquid scent including a heating element immersed in the liquid scents, and a fan to force air through said housing so that scent vapor is mixed with the air and expelled through said exhaust.

2. The invention as described in claim 1, further comprising:

a battery to power said fan and said means for heating the liquid scent.

3. The invention as described in claim 1, further comprising:

said means for heating the liquid scent including an electrical resistor located beneath said container of liquid scent.

4. The invention as described in claim 1, further comprising:

a timer circuit to cycle the scent dispenser between on and off condition.

5. The invention is described in claim 4, further comprising:

said timer circuit including a variable cycle time control.

6. The invention as described in claim 5, further comprising:

said timer circuit adapted to being switched between an on condition and an off condition by a wireless remote control unit.

7. A dispenser for scents used to attract animals, comprising:

a housing, an air inlet into said housing, an exhaust from said housing, a holder for receiving a container of liquid scent, means for heating the liquid scent, means for injecting a gas into the heated liquid scent, and a fan to force air through said housing so that scent vapor is mixed with the air and expelled through said exhaust.

8. The invention as described in claim 7, wherein said means for injecting a gas into the heated liquid scent includes feeding the gas into a conduit opening in a bottom portion of the container of liquid scent.

9. The invention as described in claim 8, further comprising a valve located in the conduit to control the injection of the gas into the liquid scent.

10. The invention as described in claim 7, wherein said means for heating the liquid scent includes a heating element immersed in the liquid scent.

* * * * *